US011109813B2

(12) United States Patent
Al Hatib et al.

(10) Patent No.: US 11,109,813 B2
(45) Date of Patent: *Sep. 7, 2021

(54) MEAN ARTERIAL PRESSURE (MAP) DERIVED PREDICTION OF FUTURE HYPOTENSION

(71) Applicant: Edwards Lifesciences Corporation, Irvine, CA (US)

(72) Inventors: Feras Al Hatib, Irvine, CA (US); Zhongping Jian, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 479 days.

This patent is subject to a terminal disclaimer.

(21) Appl. No.: 15/913,711

(22) Filed: Mar. 6, 2018

(65) Prior Publication Data

US 2018/0192962 A1    Jul. 12, 2018

Related U.S. Application Data

(63) Continuation of application No. 15/649,438, filed on Jul. 13, 2017.
(Continued)

(51) Int. Cl.
*A61B 5/00* (2006.01)
*G16H 50/30* (2018.01)
(Continued)

(52) U.S. Cl.
CPC ........ *A61B 5/7275* (2013.01); *A61B 5/02108* (2013.01); *A61B 5/6826* (2013.01);
(Continued)

(58) Field of Classification Search
None
See application file for complete search history.

(56) References Cited

U.S. PATENT DOCUMENTS

| 5,482,036 A * | 1/1996 | Diab ................. A61B 5/14551 600/364 |
| 2003/0036685 A1 * | 2/2003 | Goodman ........... G06F 19/3418 600/300 |

(Continued)

FOREIGN PATENT DOCUMENTS

| EP | 2730302 A1 | 5/2014 |
| KR | 10-2009-0049709 A | 5/2009 |

(Continued)

OTHER PUBLICATIONS

Chen, X. et al., Forecasting Acute Hypotensive Episodes in Intensive Care Patients Based on a Peripheral Arterial Blood Pressure Waveform, Computers in Cardiology 2009; 36:545-548.
(Continued)

*Primary Examiner* — Michael R Bloch
(74) *Attorney, Agent, or Firm* — Rick Nelson; David Fairbairn; Kinney & Lange

(57) ABSTRACT

There are provided systems and methods for performing mean arterial pressure (MAP) derived prediction of future hypotension. Such a system includes a hardware unit including a hardware processor and a system memory, a hypotension prediction software code stored in the system memory, and a sensory alarm. The hardware processor is configured to execute the hypotension prediction software code to receive MAP data of the living subject, and to transform the MAP data to one or more parameters predictive of a future hypotension event of the living subject. The hardware processor is further configured to execute the hypotension prediction software code to determine a risk score of the living subject corresponding to the probability of the future hypotension event based on at least some of the one or more parameters, and to invoke the sensory alarm if the risk score of the living subject satisfies a predetermined risk criteria.

13 Claims, 5 Drawing Sheets

Related U.S. Application Data

(60) Provisional application No. 62/365,815, filed on Jul. 22, 2016.

(51) Int. Cl.

| | | |
|---|---|---|
| *G16H 50/50* | (2018.01) | |
| *G16H 40/63* | (2018.01) | |
| *A61B 5/021* | (2006.01) | |
| *A61B 5/022* | (2006.01) | |

(52) U.S. Cl.
CPC .............. *A61B 5/742* (2013.01); *A61B 5/746* (2013.01); *G16H 40/63* (2018.01); *G16H 50/30* (2018.01); *G16H 50/50* (2018.01); *A61B 5/02241* (2013.01); *A61B 5/7267* (2013.01); *A61B 2505/01* (2013.01); *A61B 2505/03* (2013.01); *A61B 2505/05* (2013.01)

(56) References Cited

U.S. PATENT DOCUMENTS

| | | |
|---|---|---|
| 2005/0187796 A1 | 8/2005 | Rosenfeld et al. |
| 2008/0319332 A1 | 12/2008 | Sommo et al. |
| 2011/0245631 A1 | 10/2011 | Genc |
| 2013/0023776 A1* | 1/2013 | Olde .................. A61M 1/3656 600/487 |
| 2013/0096402 A1* | 4/2013 | Olde .................. A61B 5/02108 600/324 |
| 2013/0262357 A1 | 10/2013 | Amarasingham et al. |
| 2014/0107433 A1 | 4/2014 | Wegerich |
| 2014/0107504 A1* | 4/2014 | Stapelfeldt ........... A61B 5/4839 600/485 |
| 2014/0322225 A1* | 10/2014 | Bergmann .............. A61P 43/00 424/139.1 |
| 2014/0364750 A1 | 12/2014 | Brumfield et al. |
| 2015/0065826 A1 | 3/2015 | Mulligan et al. |
| 2015/0116333 A1 | 4/2015 | Harper et al. |
| 2015/0164437 A1 | 6/2015 | McCombie et al. |
| 2015/0282717 A1 | 10/2015 | McCombie et al. |
| 2016/0143596 A1 | 5/2016 | Bhattacharya et al. |

FOREIGN PATENT DOCUMENTS

| | | |
|---|---|---|
| WO | 2004034898 A2 | 4/2004 |
| WO | 2015183689 A1 | 12/2015 |
| WO | 2016022989 A2 | 2/2016 |

OTHER PUBLICATIONS

Chiarugi, F., Predicting the Occurrence of Acute Hypotensive Episodes: The PhysioNet Challenge; Computers in Cardiology 2009; 36:621-624.

Fournier, PA, et al., Acute Hypotension Episode Prediction Using Information Divergence for a Feature Selection, and Non-Parametric Methods for Classification; Computers in Cardiology 2009; 36:625-628.

Hayn, D., A Biosignal Analysis Applied for Developing an Algorithm Predicting Critical Situations of High Risk Cardiac Patients by Hemodynamic Monitoring; Computers in Cardiology 2009; 36: 629-632.

Henriques, JH et al., Prediction of Acute Hypotensive Episodes Using Neural Network Multi-models; Computers in Cardiology 2009; 36:549-552.

Ho, TCT et al., Utilizing Histogram to Identify Patients Using Pressors for Acute Hypotension, Computers in Cardiology 2009; 36:797-800.

Jin, K. et al., Smooting and Discriminating MAP Data; Computers in Cardiology 2009; 36: 633-636.

Jousset, F., Computers in Cardiology/Physionet Challenge 2009: Predicting Acute Hypotensive Episodes, 2009; 36:637-640.

Langley, P., et al., Predicting Acute Hypotensive Episodes From Mean Arterial Pressure; Computers in Cardiology 2009; 36: 553-556.

Mneimneh, MA, et al., A Rule-Based Approach for the Prediction of Acute Hypotensive Episodes; Computers in Cardiology 2009; 36:557-560.

Moody, GB et al.; Predicting Acute Hypotensive Episodes: The 10th Annual PhysioNet/Computers in Cardiology Challenge, 2009; 36:541-544.

* cited by examiner

MEAN ARTERIAL PRESSURE (MAP) DERIVED PREDICTION OF FUTURE HYPOTENSION

BACKGROUND

Hypotension, or low blood pressure, can be a harbinger of serious medical complications, and even mortality, for patients undergoing surgery and those acutely or critically ill patients receiving treatment in an intensive care unit (ICU). The dangers associated with the occurrence of hypotension in a patient are due both to the potential injury caused by the hypotension itself and to the many serious underlying medical disorders that the occurrence of hypotension may signify.

In and of itself, hypotension in surgical patients or critically ill patients is a serious medical condition. For example, in the operating room (OR) setting, hypotension during surgery is associated with increased mortality and organ injury. Even short durations of extreme hypotension during surgery are associated with acute kidney injury and myocardial injury. Among critically ill patients, in-hospital mortality may be nearly doubled for patients experiencing hypotension after emergency intubation. For surgical patients and seriously ill patients alike, hypotension, if not corrected, can impair organ perfusion, resulting in irreversible ischemic damage, neurological deficit, cardiomyopathy, and renal impairment.

In addition to posing serious risks to surgical patients and critically ill patients in its own right, hypotension can be a symptom of one or more other serious underlying medical conditions. Examples of underlying conditions for which hypotension may serve as an acute symptom include sepsis, myocardial infarction, cardiac arrhythmia, pulmonary embolism, hemorrhage, dehydration, anaphylaxis, acute reaction to medication, hypovolemia, insufficient cardiac output, and vasodilatory shock. Due to its association with such a variety of serious medical conditions, hypotension is relatively common, and is often seen as one of the first signs of patient deterioration in the OR and ICU. For instance, hypotension is seen in up to approximately thirty-three percent of surgeries overall, and up to eighty-five percent in high risk surgeries. Among ICU patients, hypotension occurs in from approximately twenty-four percent to approximately eighty-five percent of all patients, with the eighty-five percent occurrence being seen among critically ill patients.

Conventional patient monitoring for hypotension in the OR and ICU settings can include continuous or periodic blood pressure measurement. However, such monitoring, whether continuous or periodic, typically provides no more than a real-time assessment. As a result, hypotension in a surgical patient or critically ill patient is usually detected only after it begins to occur, so that remedial measures and interventions cannot be initiated until the patient has entered a hypotensive state. Although, as noted above, extreme hypotension can have potentially devastating medical consequences quite quickly, even relatively mild levels of hypotension can herald or precipitate cardiac arrest in patients with limited cardiac reserve.

In view of the frequency with which hypotension is observed to occur in the OR and ICU settings, and due to the serious and sometimes immediate medical consequences that can result when it does occurs, a solution enabling prediction of a future hypotension event, before its occurrence, is highly desirable.

SUMMARY

There are provided systems and methods for performing mean arterial pressure (MAP) derived prediction of future hypotension, substantially as shown in and/or described in connection with at least one of the figures, and as set forth more completely in the claims.

DETAILED DESCRIPTION

Figure 1:
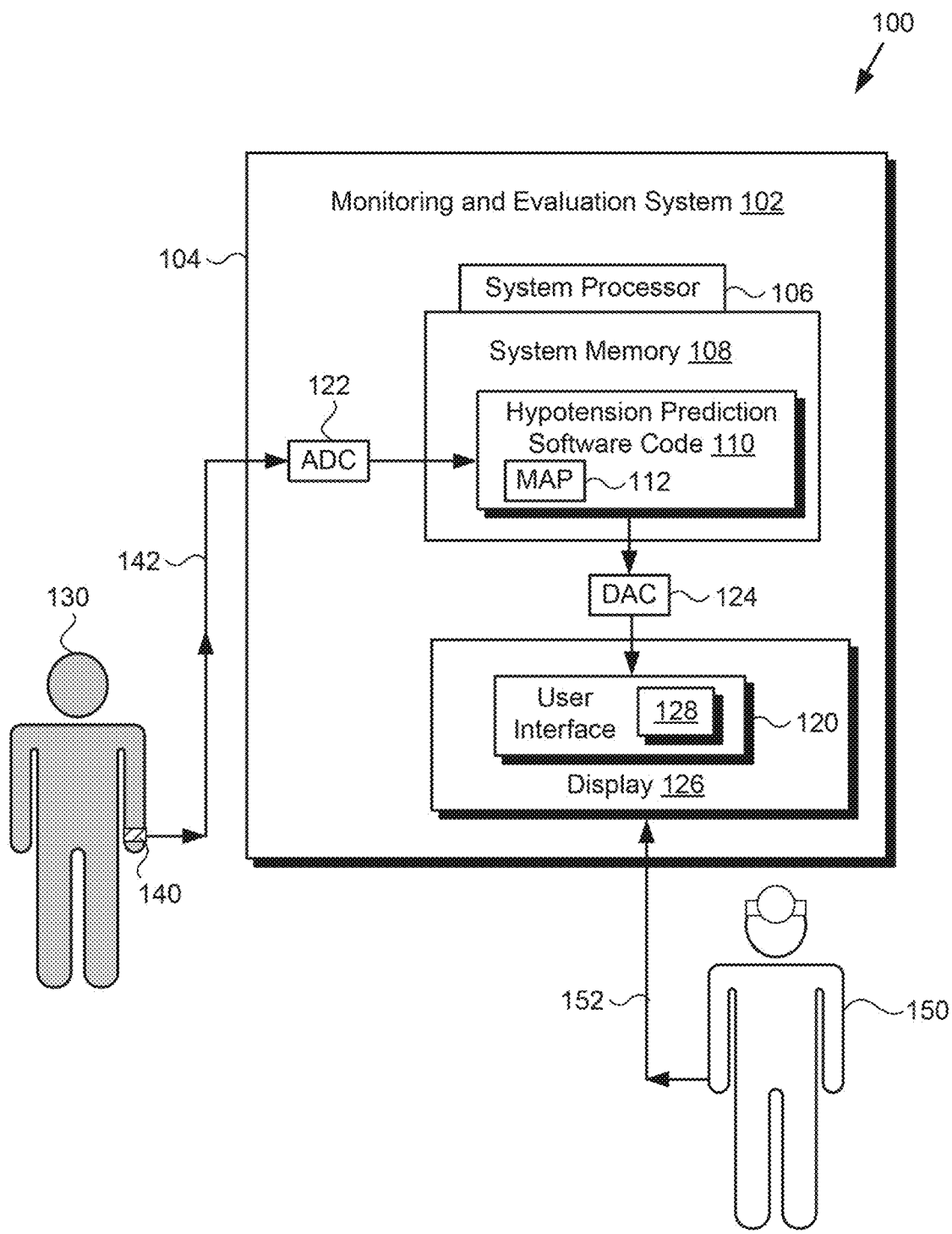
FIG. 1 shows a diagram of an exemplary system for performing mean arterial pressure (MAP) derived prediction of future hypotension, according to one implementation.

The following description contains specific information pertaining to implementations in the present disclosure. One skilled in the art will recognize that the present disclosure may be implemented in a manner different from that specifically discussed herein. The drawings in the present application and their accompanying detailed description are directed to merely exemplary implementations. Unless noted otherwise, like or corresponding elements among the figures may be indicated by like or corresponding reference numerals. Moreover, the drawings and illustrations in the present application are generally not to scale, and are not intended to correspond to actual relative dimensions.

The present application discloses systems and methods for performing mean arterial pressure (hereinafter "MAP") derived prediction of future hypotension. By transforming MAP data of a living subject to one or more parameters predictive of a future hypotension event of the living subject, the present application discloses a solution enabling determination of a risk score corresponding to the probability that the future hypotension event will occur. In addition, by receiving and transforming the MAP data of the living subject on an ongoing basis, the solution disclosed by the present application enables substantially continuous hypotension risk monitoring of the living subject. Moreover, by invoking a sensory alarm if the risk score of the living subject satisfies a predetermined risk criteria, the present application discloses a solution that provides an early warning of a future hypotension event of the living subject, thereby advantageously enabling health care workers to prepare a timely and effective intervention.

FIG. 1 shows a diagram of an exemplary system for performing MAP derived prediction of future hypotension, according to one implementation. Monitoring and evaluation system 102 is implemented within patient care environment 100, which may be an intensive care unit (ICU) or operating room (OR), for example. As shown in FIG. 1, in addition to monitoring and evaluation system 102, patient care environment 100 includes patient 130 (hereinafter "living subject 130"), and healthcare worker 150 (hereinafter "user 150") trained to utilize monitoring and evaluation system 102.

As further shown in FIG. 1, monitoring and evaluation system 102 includes system processor 106, implemented as a hardware processor, and system memory 108 storing hypotension prediction software code 110 for processing MAP data 112. Monitoring and evaluation system 102 also includes display 126 providing user interface 120. As will be discussed in greater detail below, user interface 120 is configured to receive inputs 152 from user 150, and to provide sensory alarm 128 if a risk score predictive of a future hypotension event of living subject 130 satisfies a predetermined risk criteria. Also shown in FIG. 1 are analog-to-digital converter 122 (hereinafter "ADC 122") and digital-to-analog converter 124 (hereinafter "DAC 124") used by monitoring and evaluation system 102 to process data associated with determination and display of the hypotension risk score of living subject 130.

In addition, FIG. 1 shows exemplary hemodynamic sensor 140 attached to living subject 130. It is noted that hemodynamic sensor 140 may be a non-invasive or minimally invasive sensor attached to living subject 130. In one implementation, as represented in FIG. 1, hemodynamic sensor 140 may be attached non-invasively at an extremity of living subject 130, such as a wrist or finger of living subject 130. Although not explicitly shown in FIG. 1, in other implementations, hemodynamic sensor 140 may be attached non-invasively at an ankle or toe of living subject 130. FIG. 1 further shows hemodynamic signals 142 received by monitoring and evaluation system 102, which may include signals corresponding to the arterial pressure of living subject 130. Monitoring and evaluation system 102 and hemodynamic sensor 140 may be configured such that hemodynamic signals 142 may be received by monitoring and evaluation system 102 wirelessly, or via a wired connection with hemodynamic sensor 140.

System processor 106 is configured to execute hypotension prediction software code 110 to receive MAP data 112 of living subject 130. System processor 106 is further configured to execute hypotension prediction software code 110 to transform MAP data 112 to one or more parameters predictive of a future hypotension event by living subject 130. For example, hypotension prediction software code 110 may transform MAP data 112 to one or more parameters predictive of a hypotension event by living subject 130 occurring in the next approximately one to five minutes, or up to approximately thirty minutes in the future.

System processor 106 is also configured to execute hypotension prediction software code 110 to determine a risk score of living subject 130 corresponding to the probability of the future hypotension event based on at least some, i.e., at least a subset, of the one or more parameters derived from MAP data 112. In addition, system processor 106 is configured to execute hypotension prediction software code 110 to invoke sensory alarm 128 if the risk score of living subject 130 satisfies a predetermined risk criteria.

In various implementations, sensory alarm 128 may be implemented as one or more of a visual alarm, an audible alarm, and a haptic alarm. For example, when implemented to provide a visual alarm, sensory alarm 128 may be invoked as flashing and/or colored graphics shown by user interface 120 on display 126, and/or may include displaying the risk score via user interface 120 on display 126. When implemented to provide an audible alarm, sensory alarm 128 may be invoked as any suitable warning sound, such as a siren or repeated tone. Moreover, when implemented to provide a haptic alarm, sensory alarm 128 may cause hardware unit 104 to vibrate or otherwise deliver a physical impulse perceptible to user 150.

It is noted that the risk score of living subject 130 is determined based on parameters derived from MAP data 112 of living subject 130, which in turn is determined based on hemodynamic signals 142 of living subject 130 received from hemodynamic sensor 140. Consequently, according to the inventive concepts disclosed by the present application, hardware processor 106 of monitoring and evaluation system 102 is configured to execute hypotension prediction software code 110 to determine the risk score of living subject 130 without comparison with data corresponding to hypotension in other living subjects. In other words, hypotension prediction software code 110 determines the risk score of living subject 130 based on parameters derived from MAP data 112 without reference to a hypotension patient database storing information regarding hypotension in patients other than living subject 130.

In addition to the functionality described above, in some implementations, hardware processor 106 may be configured to execute hypotension prediction software code 110 to identify a most probable cause of the future hypotension event of living subject 130. For example, based on indicia included in hemodynamic signals 142, hypotension prediction software code 110 may be able to identify poor vascular tone, low blood volume, or reduced cardiac contractility, to name a few exemplary causes, as a most probable cause of a predicted future hypotension event. Furthermore, in some implementations, hardware processor 106 may be configured to execute hypotension prediction software code 110 to recommend a medical intervention for preventing the future hypotension event of living subject 130. With respect to the first and second example causes of hypotension identified above, administration of a vasoconstrictor may be recommended if poor vascular tone is detected, while administration of saline or whole blood may be recommend if low blood volume is identified as a most probable cause of the predicted future hypotension event. In one implementation, system 102 may automatically administer the medical intervention for preventing the future hypotension event of living subject 130. For example, in response to detecting a future hypotension event, system 102 may transmit a signal causing an administration of a vasoconstrictor if poor vascular tone is detected ort causing an administration of saline or whole blood if low blood volume is identified as the issue.

Figure 2A:
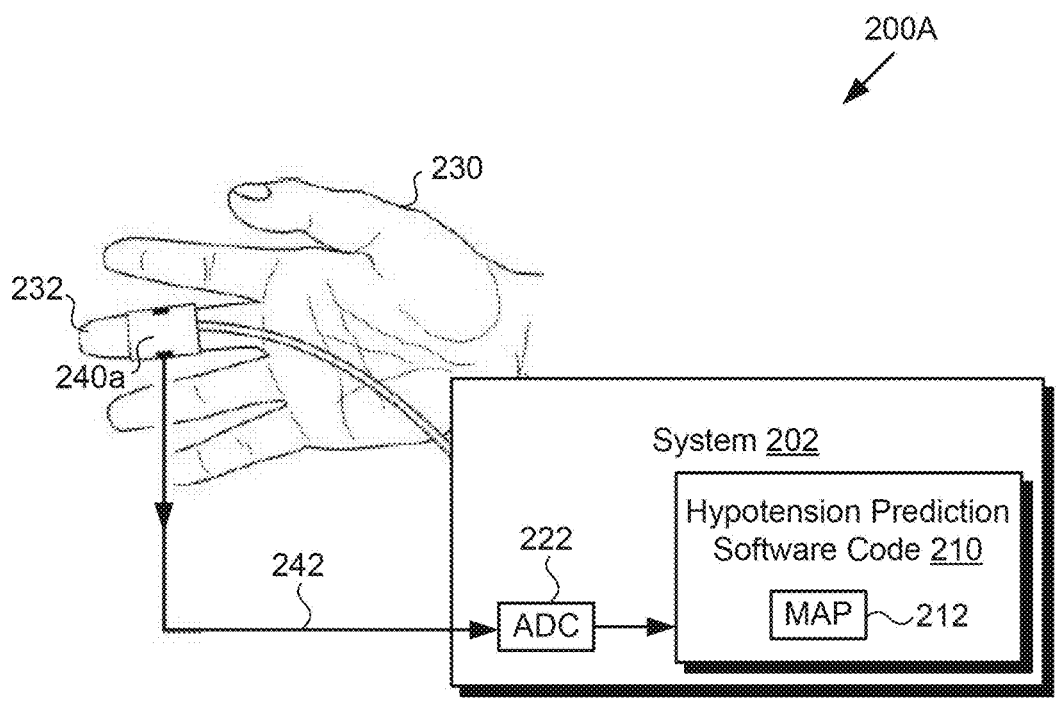
FIG. 2A shows an exemplary implementation for non-invasively detecting arterial pressure at an extremity of a living subject.

Referring to FIG. 2A, FIG. 2A shows an exemplary implementation for sensing arterial pressure non-invasively at an extremity of a living subject. Patient care environment 200A, in FIG. 2A, shows system 202 including hypotension prediction software code 210 receiving MAP data 212 of living subject 230. As further shown by FIG. 2A, the arterial pressure of living subject 230 is detected non-invasively at finger 232 of living subject 230 using hemodynamic sensing cuff 240a. Also shown in FIG. 2A are ADC 222 of system 202, and hemodynamic signals 242 received by system 202 from hemodynamic sensing cuff 240a.

Living subject 230, hemodynamic signals 242, and hemodynamic sensing cuff 240a correspond respectively in general to living subject 130, hemodynamic signals 142, and hemodynamic sensor 140, in FIG. 1, and may share any of the characteristics attributed to those corresponding features in the present application. Moreover, system 202 including ADC 222 and hypotension prediction software code 210 receiving MAP data 212, in FIG. 2A, corresponds in general to monitoring and evaluation system 102 including ADC 122 and hypotension prediction software code 110 receiving MAP data 112, in FIG. 1, and may share any of the characteristics attributed to that corresponding feature in the present application.

According to the implementation shown in FIG. 2A, hemodynamic sensing cuff 240a is designed to sense an arterial pressure of living subject 230 non-invasively at finger 232 of living subject 230. Moreover, as shown in FIG. 2A, hemodynamic sensing cuff 240a may take the form of a small, lightweight, and comfortable hemodynamic sensor suitable for extended wear by living subject 230. It is noted that although hemodynamic sensing cuff 240a is shown as a finger cuff, in FIG. 2A, in other implementations, hemodynamic sensing cuff 240a may be suitably adapted as a wrist, ankle, or toe cuff for attachment to living subject 230.

It is further noted that the advantageous extended wear capability described above for hemodynamic sensing cuff 240 when implemented as a finger cuff may also be attributed to wrist, ankle, and toe cuff implementations. As a result, hemodynamic sensing cuff 240a may be configured to provide substantially continuous beat-to-beat monitoring of the arterial pressure of living subject 230 over an extended period of time, such as minutes or hours, for example.

Figure 2B:
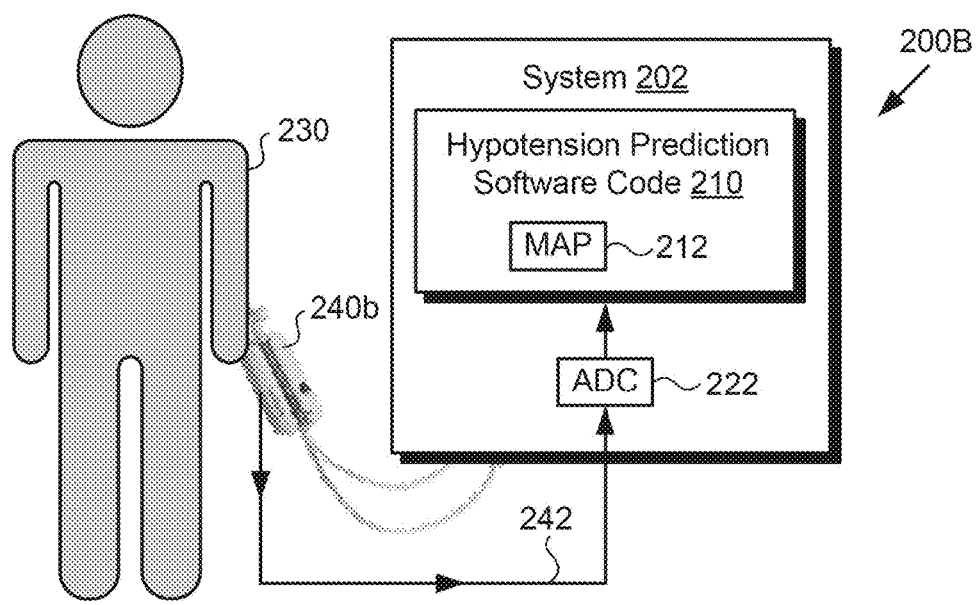
FIG. 2B shows an exemplary implementation for performing minimally invasive detection of arterial pressure of a living subject.

Continuing to FIG. 2B, FIG. 2B shows an exemplary implementation for performing minimally invasive detection of arterial pressure of a living subject. Patient care environment 200B, in FIG. 2B, shows system 202 including hypotension prediction software code 210 receiving MAP data 212 of living subject 230. As further shown by FIG. 2B, the arterial pressure of living subject 230 is detected via minimally invasive hemodynamic sensor 240b. Also shown in FIG. 2B are ADC 222 of system 202, and hemodynamic signals 242 received by system 202 from hemodynamic sensing cuff 240b.

It is noted that the features shown in FIG. 2B and identified by reference numbers identical to those shown in FIG. 2A correspond respectively to those previously described features, and may share any of the characteristics attributed to them above. It is further noted that hemodynamic sensor 240b corresponds in general to hemodynamic sensor 140, in FIG. 1, and may share any of the characteristics attributed to that corresponding feature in the present application.

According to the implementation shown in FIG. 2B, hemodynamic sensor 240b is designed to sense an arterial pressure of living subject 230 in a minimally invasive manner. For example, hemodynamic sensor 240b may be attached to living subject 230 via a radial arterial catheter inserted into an arm of living subject 230. Alternatively, and although not explicitly represented in FIG. 2B, in another implementation, hemodynamic sensor 240b may be attached to living subject 230 via a femoral arterial catheter inserted into a leg of living subject 230. Like non-invasive hemodynamic sensing cuff 240a, in FIG. 2A, minimally invasive hemodynamic sensor 240b, in FIG. 2B, may be configured to provide substantially continuous beat-to-beat monitoring of the arterial pressure of living subject 230 over an extended period of time, such as minutes or hours, for example.

Figure 3:
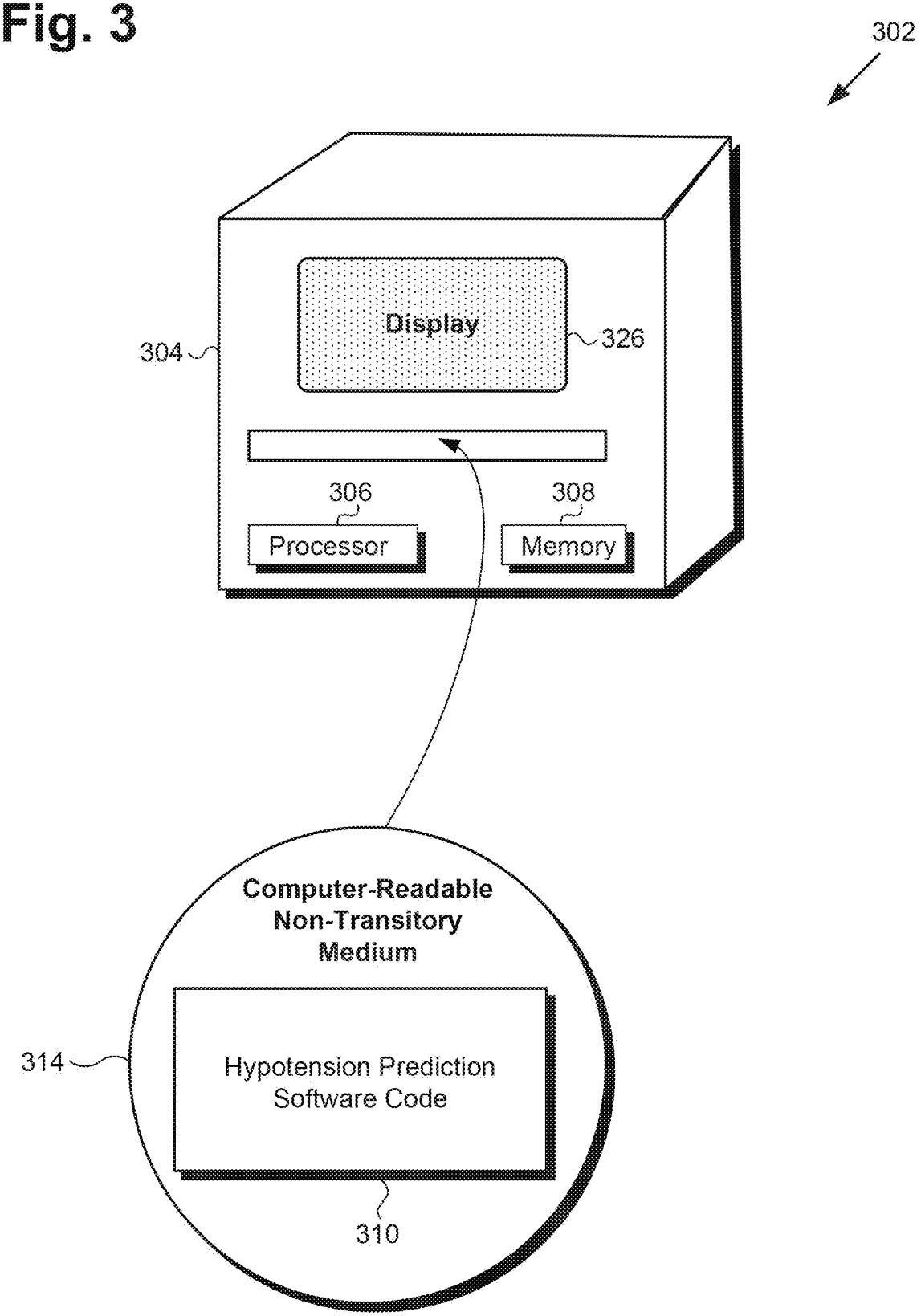
FIG. 3 shows an exemplary system and a computer-readable non-transitory medium including instructions enabling performance of MAP derived prediction of future hypotension.

Moving now to FIG. 3, FIG. 3 shows an exemplary system and a computer-readable non-transitory medium including instructions enabling performance of MAP derived prediction of future hypotension. System 302, in FIG. 3, includes hardware unit 304 including processor 306, memory 308, and display 326. Display 326 may take the form of a liquid crystal display (LCD), a light-emitting diode (LED) display, an organic light-emitting diode (OLED) display, or another suitable display screen that performs a physical transformation of signals to light. System 302 including hardware unit 304 having processor 306 and memory 308 corresponds in general to monitoring and evaluation system 102 including hardware unit 104 having system processor 106 and system memory 108, and may share any of the characteristics attributed to that corresponding feature in the present application. That is to say, system 302 may be configured to provide user interface 120 and/or sensory alarm 128 using display 326.

Also shown in FIG. 3 is computer-readable non-transitory medium 314 having hypotension prediction software code 310 stored thereon. The expression "computer-readable non-transitory medium," as used in the present application, refers to any medium, excluding a carrier wave or other transitory signal, that provides instructions to processor 306 of system 302. Thus, a computer-readable non-transitory medium may correspond to various types of media, such as volatile media and non-volatile media, for example. Volatile media may include dynamic memory, such as dynamic random access memory (dynamic RAM), while non-volatile memory may include optical, magnetic, or electrostatic storage devices. Common forms of computer-readable non-transitory media include, for example, optical discs, RAM, programmable read-only memory (PROM), erasable PROM (EPROM), and FLASH memory.

According to the implementation shown in FIG. 3, computer-readable non-transitory medium 314 provides hypotension prediction software code 310 for execution by processor 306 of system 302. Hypotension prediction software code 310, when executed by processor 306, instantiates a hypotension prediction software code corresponding to hypotension prediction software code 110/210, in FIG. 1/2, and capable of performing all of the operations performed by that corresponding feature and described in the present application.

Figure 4:
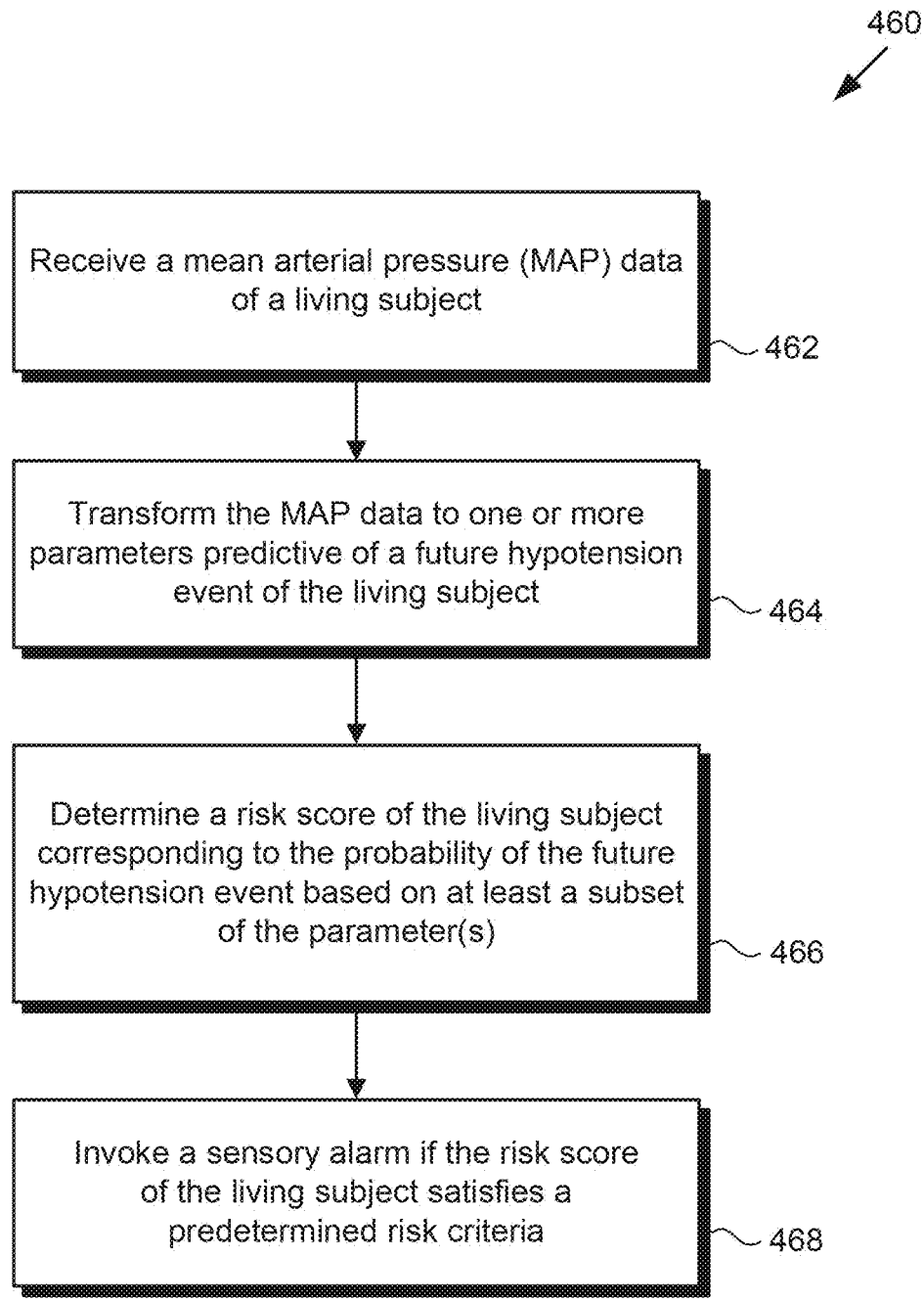
FIG. 4 is a flowchart presenting an exemplary method for use by a monitoring and evaluation system to perform MAP derived prediction of future hypotension.
Figure 5:
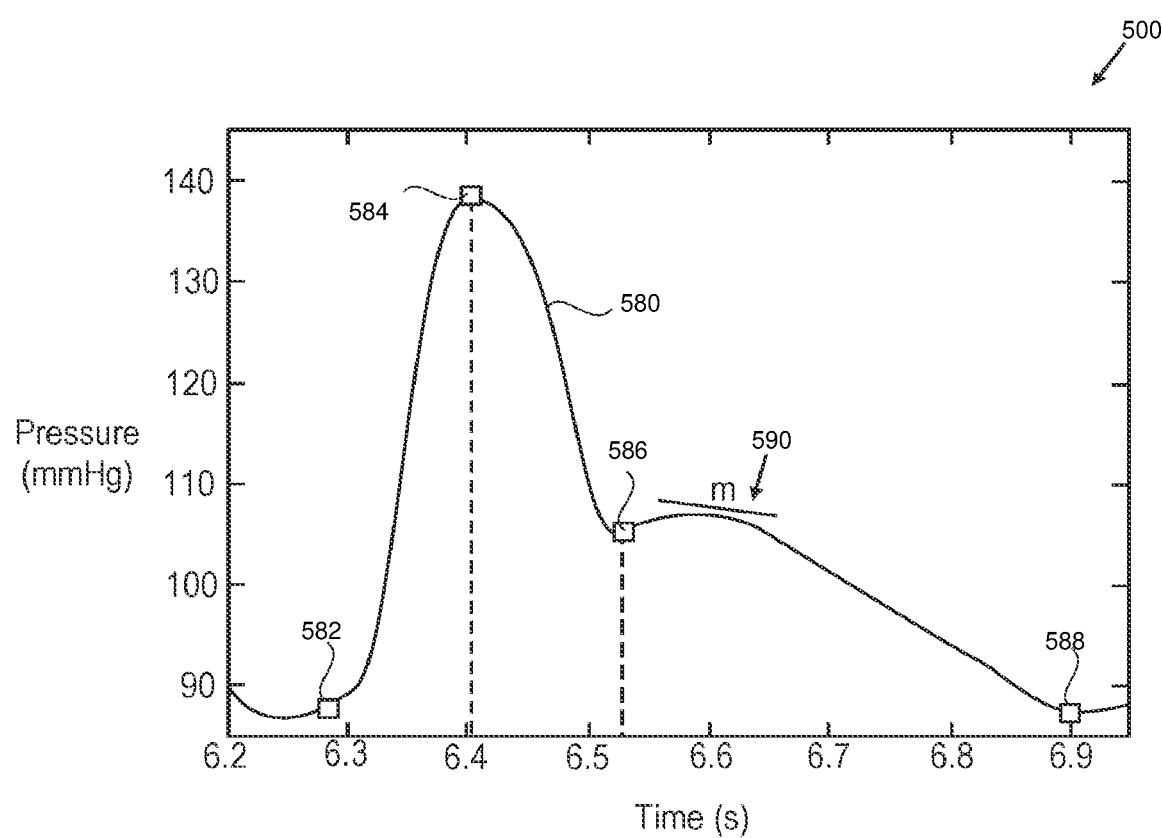
FIG. 5 shows a trace of an arterial pressure waveform including exemplary is indicia corresponding to the probability of future hypotension in a living subject.

Example implementations of the present inventive concepts will be further described below with reference to FIG. 4 and FIG. 5. FIG. 4 presents flowchart 460 outlining an exemplary method for use by a monitoring and evaluation system to perform MAP derived prediction of future hypotension, while FIG. 5 shows a trace of an arterial pressure waveform including exemplary indicia corresponding to the probability of future hypotension in a living subject. The method outlined in flowchart 400 can be performed using hypotension prediction software code 110/210/310 described above.

Flowchart 460 begins with receiving, by hypotension prediction software code 110/210/310 executed by processor 106/306, MAP data 112/212 of living subject 130/230 (action 462). As used herein, the expression "MAP data" refers to data utilized to determine the mean arterial pressure or MAP of a living subject, as well as data derived from predictive indicia and enabling prediction of future hypotension in the living subject based on the MAP of the living subject. For example, MAP data 112/212 may be extracted and/or processed from hemodynamic signals 142/242 received by system 102/202/302 from hemodynamic sensor 140/240a/240b.

In one implementation, for example, hemodynamic sensor 140/240a/240b may be used to sense an arterial pressure of living subject 130/230 at an extremity of living subject 130/230, and to determine a central arterial pressure of living subject 130/230 based on the sensed arterial pressure. System 102/202/302 may be configured to receive the determined central arterial pressure of living subject 130/230 as hemodynamic signals 142/242, which, in various implementations, may be received as analog signals or digital signals. In implementations in which hemodynamic signals 142/242 are received as analog signals, system 102/202/302 utilizes ADC 122 to convert hemodynamic signals 142/242 into digital data including MAP data 112/212. It is noted that in other implementations, system 102/202/302 can be configured to determine the central arterial pressure of living subject 130/230 based on the arterial pressure sensed by hemodynamic sensor 140/240a/240b.

Referring to diagram 500, in FIG. 5, MAP data 112/212 may include various indicia predictive of future hypotension in living subject 130/230 and derived from arterial pressure waveform 580, which may be a central arterial pressure waveform of living subject 130/230, for example. Diagram 500 shows exemplary indicia 582, 584, 586, and 588, corresponding respectively to the start of a heartbeat, the maximum systolic pressure marking the end of systolic rise, the presence of the dicrotic notch marking the end of systolic decay, and the diastole of the heartbeat of living subject 130/230. Also shown by diagram 500 is exemplary slope 590 of arterial pressure waveform 580. It is noted that slope 590 is merely representative of multiple slopes that may be measured at multiple locations along arterial pressure waveform 580.

In addition to the indicia 582, 584, 586, and 588 of arterial pressure waveform 580 per se, the behavior of arterial pressure waveform 580 during the intervals between those indicia may also be used as indicia predictive of future hypotension for living subject 130/240. For example, the interval between the start of the heartbeat at indicia 582 and the maximum systolic pressure at indicia 584 marks the duration of the systolic rise (hereinafter "systolic rise 582-584"). The systolic decay of arterial pressure waveform 580 is marked by the interval between the maximum systolic pressure at indicia 584 and the dicrotic notch at indicia 586 (hereinafter "systolic decay 584-586"). Together, systolic rise 582-584 and systolic decay 584-586 mark the entire systolic phase (hereinafter "systolic phase 582-586"), while the interval between the dicrotic notch at indicia 586 and the diastole at indicia 588 mark the diastolic phase of arterial pressure waveform 580 (hereinafter "diastolic phase 586-588").

Also of potential diagnostic interest is the behavior of arterial pressure waveform 580 in the interval from the maximum systolic pressure at indicia 584 to the diastole at indicia 588 (hereinafter "interval 584-588"), as well as the behavior of arterial pressure waveform 580 from the start of the heartbeat at indicia 582 to the diastole at indicia 588 (hereinafter "heartbeat interval 582-588"). The behavior of arterial pressure waveform 580 during intervals: 1) systolic rise 582-584, 2) systolic decay 584-586, 3) systolic phase 582-586, 4) diastolic phase 586-588, 5) interval 584-588, and 6) heartbeat interval 582-588 may be determined by measuring the area under the curve of arterial pressure waveform 580 and the standard deviation of arterial pressure waveform 580 in each of those intervals, for example. The respective areas and standard deviations measured for intervals 1, 2, 3, 4, 5, and 6 above (hereinafter "intervals 1-6") may serve as additional indicia predictive of future hypotension for living subject 130/240.

As noted above, MAP data 112/212 may include any or all of indicia 582, 584, 586, 588, and 590, as well as the respective areas and standard deviations measured for intervals 1-6 of arterial pressure waveform 580, and may be utilized to determine MAP itself, or to enable prediction of future hypotension in living subject 130/230 based on MAP.

With respect to determination of MAP itself, as known in the art, MAP may be determined from the following equation:

$$\text{MAP} = (\text{CO}*\text{SVR}) + \text{CVP} \quad \text{(Equation 1)}$$

where CO is cardiac output, SVR is systemic vascular resistance, and CVP is central venous pressure. However, MAP may also be approximately determined using systolic pressure (SP) and diastolic pressure (DP), corresponding respectively to maximum systolic pressure 584 and pressure at diastole 588. According to such an approximate determination, MAP may be expressed as:

$$\text{MAP(approximately)} = \text{DP} + \tfrac{1}{3}(\text{SP} - \text{DP}) \quad \text{(Equation 2)}$$

Thus, in one implementation, MAP data 112/212 may include at least data corresponding to indicia 584 and 588 for generating an approximate determination of MAP. However, in other implementations, MAP data 112/212 may include data extracted and/or processed from hemodynamic signals 142/242 and corresponding to the cardiac output (CO), systemic vascular resistance (SVR), and central venous pressure (CVP) of living subject 130/230.

Flowchart 460 continues with transforming, by hypotension prediction software code 110/210/310 executed by processor 106/306, MAP data 112/212 to at least one parameter predictive of a future hypotension event of living subject 130/230 (action 464). For example, in one implementation, MAP itself may be a single parameter sufficient to predict a future hypotension event of living subject 130/230. Specifically, in one implementation, a future hypotension event by living subject 130/230 may be predicted based on MAP by the following equation:

$$\text{Risk Score} = 1/(1 + e^{-((a*\text{MAP}) + b)}) \quad \text{(Equation 3)}$$

where Risk Score corresponds to the probability of a future hypotension event of living subject 130/230, and "a", MAP itself, and "b", are parameters predictive of such a hypotensive event. It is noted that in some implementations, the parameters "a" and "b" may be predetermined and fixed, while in other implementations, "a" and "b" may be variables that are determined on a case-by-case basis and may be obtained from the transformation of MAP data 112/212 performed as action 464.

Flowchart 460 continues with determining, by hypotension prediction software code 110/210/310 executed by processor 106/306, the risk score for living subject 130/230, e.g., Risk Score above (action 466). As noted above, the risk score for living subject 130/230 may be determined using Equation 3. In some implementations, the risk score may be expressed as a fraction, as represented by Equation 3. However, in some implementations, the risk score may be converted to a percentage risk score between zero percent and one hundred percent.

It is emphasized that the risk score of living subject 130/230 is determined based on parameters derived from MAP data 112/212 of living subject 130/230, which in turn is determined based on hemodynamic signals 142/242 of living subject 130/230 received from hemodynamic sensor 140/240a/240b. Consequently, according to the inventive concepts disclosed by the present application, hardware processor 106/306 is configured to execute hypotension prediction software code 110/210/310 to determine the risk score of living subject 130/230 without comparison with data corresponding to hypotension in other living subjects. That is to say, hypotension prediction software code 110/210/310 determines the risk score of living subject 130/230 based on parameters derived from MAP data 112/212 without reference to a hypotension patient database storing information regarding hypotension in patients other than living subject 130/230.

Flowchart 460 can conclude with invoking, by hypotension prediction software code 110/210/310 executed by processor 106/306, sensory alarm 128 if the risk score of living subject 130/230 satisfies a predetermined risk criteria (action 468). As shown in FIG. 1, for example, hypotension prediction software code 110/210/310 may be configured to provide an output to user interface 120 on display 126/326 for displaying the risk score of living subject 130/230, and/or for invoking sensory alarm 128. As further shown in FIG. 1, in some implementations, the output of hypotension prediction software code 110/210/310 may be processed using DAC 124 to convert digital signals into analog signals for presentation via user interface 120.

The predetermined risk criteria may be based on the value of the risk score, on the trend of the risk score over a time interval, or both. For example, where the risk score is expressed as a percentage between zero and one hundred, having the risk score exceed a threshold of eighty-five percent, for instance, may cause sensory alarm 128 to be invoked immediately. Alternatively, or in addition, a lower risk score may cause sensory alarm 128 to be invoked if it exceeds a predetermined threshold over the entirety of a predetermined time period.

Thus, for example, while a risk score of eighty five percent may cause sensory alarm 128 to be invoked immediately, a risk score of eighty percent may cause sensory alarm 128 to be invoked after several seconds at that level, such as ten to thirty seconds in which the risk score is continuously between eighty and eighty five percent, for example. By analogy, a still lower risk score may cause sensory alarm 128 to be invoked if that risk score is maintained continuously for one or more minutes. In yet another implementation, the risk score may cause sensory alarm 128 to be invoked if it meets or exceeds a predetermined value a predetermined number of times over a predetermined time period. For example, having the risk score exceed seventy five percent three times over a five minute interval may cause sensory alarm 128 to be invoked.

As noted above by reference to FIG. 1, sensory alarm 128 may be implemented as one or more of a visual alarm, an audible alarm, and a haptic alarm. For example, when implemented to provide a visual alarm, sensory alarm 128 may be invoked as flashing and/or colored graphics shown by user interface 120 on display 126, and/or may include displaying the risk score via user interface 120 on display 126/326. When implemented to provide an audible alarm, sensory alarm 128 may be invoked as any suitable warning sound, such as a siren or repeated tone. Moreover, when implemented to provide a haptic alarm, sensory alarm 128 may cause hardware unit 104/304 to vibrate or otherwise deliver a physical impulse perceptible to user 150.

Although not included among the actions outlined by flowchart 460, in some implementations, the present method may include identifying, by hypotension prediction software code 110/210/310 executed by processor 106/306, a most probable cause of the future hypotension event of living subject 130/230. For example, and as noted above, based on indicia included in hemodynamic signals 142, hypotension prediction software code 110/210/310 may be used to identify poor vascular tone, low blood volume, or reduced cardiac contractility, to name a few exemplary causes, as a most probable cause of a predicted future hypotension event.

In addition, in some implementations, the present method may include recommending, by hypotension prediction software code 110/210/310 executed by processor 106/306, a medical intervention for preventing the future hypotension event of living subject 130/230. With respect to poor vascular tone or low blood volume, for example, administration of a vasoconstrictor may be recommended if poor vascular tone is detected, while administration of saline or whole blood may be recommend if low blood volume is identified as a most probable cause of the predicted future hypotension event.

Thus, by transforming MAP data of a living subject to one or more parameters predictive of a future hypotension event of the living subject, the present application discloses a solution enabling determination of a risk score corresponding to the probability that the future hypotension event will occur. In addition, by receiving and transforming the MAP data of the living subject on an ongoing basis, the solution disclosed by the present application enables substantially continuous hypotension risk monitoring of the living subject. Moreover, by invoking a sensory alarm if the risk score of the living subject satisfies a predetermined risk criteria, the present application discloses a solution that provides an early warning of a future hypotension event of the living subject, thereby advantageously enabling health care workers to prepare a timely and effective intervention.

From the above description it is manifest that various techniques can be used for implementing the concepts described in the present application without departing from the scope of those concepts. Moreover, while the concepts have been described with specific reference to certain implementations, a person of ordinary skill in the art would recognize that changes can be made in form and detail without departing from the scope of those concepts. As such, the described implementations are to be considered in all respects as illustrative and not restrictive. It should also be understood that the present application is not limited to the particular implementations described herein, but many rearrangements, modifications, and substitutions are possible without departing from the scope of the present disclosure.

What is claimed is:

1. A system for monitoring and evaluation of a living subject, the system comprising:
    hemodynamic sensor configured to be attached to the living subject, sense an arterial pressure of the living subject, and generate a hemodynamic signal based on the arterial pressure of the living subject;
    an analog-to-digital converter configured to receive the hemodynamic signal and convert the hemodynamic signal to hemodynamic data in digital form;
    a display;
    a system memory storing a hypotension prediction software code; and
    a hardware processor configured to execute the hypotension prediction software code to:
        determine mean arterial pressure (MAP) of the living subject based on the hemodynamic data;
        determine a risk score of the living subject corresponding to a probability of the future hypotension event, wherein the risk score is determined by the hardware processor based upon MAP, and wherein the risk score is determined by a formula: risk score=$1/(1+e^{-((a*MAP)+b)})$, where a and b are numbers; and
        display the risk score of the living subject on the display.

2. The system of claim 1 further comprising:
    a sensory alarm;
    wherein the hardware processor is configured to execute the hypotension prediction software code to invoke the sensory alarm if the risk score of the living subject satisfies a predetermined risk criteria.

3. The system of claim 2, wherein the sensory alarm is one of visual alarm, an audible alarm, and a haptic alarm.

4. The system of claim 3, wherein the visual alarm causes the risk score to be displayed on the display.

5. The system of claim 1, wherein the hardware processor is configured to execute the hypotension prediction software code to determine the risk score of the living subject without comparison with data corresponding to hypotension in other living subjects.

6. The system of claim 1, wherein the hardware processor is configured to convert the risk score to a percentage risk score between zero percent and one hundred percent for display on the display.

7. The system of claim 1, wherein a and b are fixed numbers.

8. The system of claim 1, wherein a and b are variable numbers.

9. The system of claim 1, wherein the hemodynamic signal is obtained non-invasively from the living subject.

10. The system of claim 9, wherein the hemodynamic signal is obtained non-invasively at an extremity of the living subject.

11. The system of claim 1, wherein the hardware processor is configured to calculate a cardiac output (CO), a systemic vascular resistance (SVR), and a central venous pressure (CVP) using the hemodynamic data, and is configured to determine the MAP in accordance with MAP=(CO*SVR)+CVP.

12. The system of claim 1, wherein the hardware processor is configured to calculate a systolic pressure (SP), and a diastolic pressure (DP) using the hemodynamic data, and is configured to determine the MAP in accordance with MAP (approximately)=(DP+⅓(SP−DP).

13. The system of claim 1, wherein the hardware processor is configured to display the risk score as a fraction on the display.

* * * * *